(12) United States Patent
Izatt et al.

(10) Patent No.: US 9,517,006 B2
(45) Date of Patent: Dec. 13, 2016

(54) SYSTEMS AND METHODS FOR OBTAINING LOW-ANGLE CIRCUMFERENTIAL OPTICAL ACCESS TO THE EYE

(71) Applicant: Duke University, Durham, NC (US)

(72) Inventors: Joseph A. Izatt, Raleigh, NC (US); Anthony N. Kuo, Durham, NC (US); Ryan P. McNabb, Durham, NC (US)

(73) Assignee: Duke University, Durham, NC (US)

( * ) Notice: Subject to any disclaimer, the term of this patent is extended or adjusted under 35 U.S.C. 154(b) by 78 days.

(21) Appl. No.: 14/372,599

(22) PCT Filed: Jan. 24, 2013

(86) PCT No.: PCT/US2013/022913
§ 371 (c)(1),
(2) Date: Jul. 16, 2014

(87) PCT Pub. No.: WO2013/112700
PCT Pub. Date: Aug. 1, 2013

(65) Prior Publication Data
US 2014/0354951 A1    Dec. 4, 2014

Related U.S. Application Data

(60) Provisional application No. 61/590,052, filed on Jan. 24, 2012.

(51) Int. Cl.
*A61B 3/10* (2006.01)
*G01B 9/02* (2006.01)
*A61B 3/117* (2006.01)

(52) U.S. Cl.
CPC .............. *A61B 3/102* (2013.01); *A61B 3/117* (2013.01); *G01B 9/02004* (2013.01);
(Continued)

(58) Field of Classification Search
CPC ....... A61B 3/102; A61B 3/117; A61B 3/1025; A61B 3/125; G01B 9/02004; G01B 9/02058; G01B 2290/65; G02B 9/02091
(Continued)

(56) References Cited

U.S. PATENT DOCUMENTS

2004/0196431 A1* 10/2004 Farberov ................ A61B 3/117
351/205
2008/0015553 A1    1/2008 Zacharias
(Continued)

FOREIGN PATENT DOCUMENTS

WO    2013/112700    8/2013

OTHER PUBLICATIONS

International Search Report, International Application No. PCT/US2013/022913, May 30, 2013 (3 pages).
(Continued)

*Primary Examiner* — Bumsuk Won
*Assistant Examiner* — Grant Gagnon
(74) *Attorney, Agent, or Firm* — Michael Best & Friedrich LLP (57) ABSTRACT

A system for obtaining low-angle circumferential optical access to an eye of a subject. The system includes a light source to generate a beam of light; a beam steering mechanism to steer the beam of light a focusing lens to focus the beam of light; and a contact lens to direct the beam of light into the eye of the subject, the contact lens including a tapered reflective surface to direct the beam of light into the eye of the subject.

20 Claims, 7 Drawing Sheets

(52) U.S. Cl.
CPC ..... *G01B 9/02058* (2013.01); *G01B 9/02091* (2013.01); *G01B 2290/65* (2013.01)

(58) Field of Classification Search
USPC .................................. 351/205, 206, 210, 219
See application file for complete search history.

(56) References Cited

U.S. PATENT DOCUMENTS

| | | | | |
|---|---|---|---|---|
| 2010/0091244 | A1* | 4/2010 | Volk | A61B 3/125 351/219 |
| 2011/0202044 | A1* | 8/2011 | Goldshleger | A61B 3/102 606/4 |
| 2011/0245814 | A1* | 10/2011 | Taboada | A61F 9/008 606/4 |

OTHER PUBLICATIONS

<http://www.octnews.org/articles/555937/carl-zeiss-meditec-largest-base-of-optical-coheren/?&rand=572> Accessed on Apr. 4, 2012.
Allingham et al., "Schlemm's canal and primary open angle glaucoma: correlation between Schlemm's canal dimensions and outflow facility," Exp Eye Res., 1996, 62(1):101-9.
Bizheva et al., "In vivo volumetric imaging of the human corneoscleral limbus with special domain OCT," Biomed Opt Express, 2011, 2(7):1794-02.
Tektas et al., "Structural changes of the trabecular meshwork in different kinds of glaucoma," Exp Eye Res., 2009, 88(4):769-75.
Francis et al., "Novel glaucoma procedures: a report by the American Academy of Ophthalmology," Ophthalmology, 2011, 118(7):1466-80.
Gordon et al., "The Ocular Hypertension Treatment Study: baseline factors that predict the onset of primary open-angle glaucoma," Arch Ophthalmol, 2002, 120(6):714-20, discussion 829-30.
He et al., "Femtosecond laser-assisted cataract surgery," Curr Opin Ophthalmol., 2011, 22(1):43-52.
Izatt et al., "In Vivo Biodirectional Color Doppler Flow Imaging of Picoliter Blood vols. Using Optical Coherence Tomography," Optics Letters, 1997, 22:1439-1441.
Junglas et al., "Connective tissue growth factor induces extracellular matrix deposition in human trabecular meshwork cells," Exp Eye Res., 2009, 88(6):1065-75.
Kagemann et al., "3D visualization of aqueous humor outflow structures in-situ in humans," Exp Eye Res., 2011, 93 (3):308-15.
Kass et al., "The Ocular Hypertension Treatment Study: a randomized trial determines that topical ocular hypotensive medication delays or prevents the onset of primary open-angle glaucoma," Arch Ophthalmol., 2002, 120(6):701-13, discussion 829-30.
Latina et al., "Selective laser trabeculoplasty," Ophthalmol Clin North Am., 2005, 18(3):409-19.
Li et al., "In vivo microstructural and microvascular imaging of the human corneo-scleral limbus using optical coherence tomography," Biomed Opt Express, 2011, 2(11):3109-18.
Liang et al., "Dynamic spectral-domain optical coherence elastopraphy for tissue characterization," Opt Express., 2010, 18(13):14183-90.
Quigley et al., "The number of people with glaucoma worldwide in 2010 and 2020," Br J Ophthalmol., 2006, 90 (3):262-7.

* cited by examiner

SYSTEMS AND METHODS FOR OBTAINING LOW-ANGLE CIRCUMFERENTIAL OPTICAL ACCESS TO THE EYE

CROSS-REFERENCE TO RELATED APPLICATIONS

This application is a national stage filing under 35 U.S.C. 371 of International Patent Application No. PCT/US2013/022913, filed Jan. 24, 2013, which claims the benefit of priority to U.S. Provisional Patent Application No. 61/590,052, filed Jan. 24, 2012, the contents of which are incorporated herein by reference in their entireties.

GOVERNMENT SUPPORT

This invention was made with government support under Grant Nos.: K23-EY021522, R21-EY020001, and K12-EY016333 awarded by the National Institutes of Health. The government has certain rights in the invention.

BACKGROUND

The present invention relates to methods and systems for obtaining low-angle circumferential optical access to the eye.

Resistance in the ocular pathway results in elevated intraocular pressure (IOP), one of the most important risk factors for the development of vision-threatening glaucomatous changes. All current glaucoma therapeutics lower IOP to prevent further neuronal death from this blinding disease.

Many of the clinically most vulnerable elements of the outflow pathway (trabecular meshwork, Canal of Schlemm, collector channels, and other distal structures) cannot be imaged using conventional medical imaging modalities. These elements cannot be imaged with routine clinical ultrasound, computed tomography (CT) or magnetic resonance imaging (MRI) because the structures are too small (submillimeter) to be resolved with these techniques. These elements cannot be imaged using standard optical microscopy and can only be imaged in a limited fashion with optical coherence tomography (OCT) from the outside of the eye because they are located behind the translucent sclera, which completely obscures standard microscopy and substantially reduces the resolution and signal-to-noise ratio of standard anterior segment OCT. These elements cannot be readily imaged from inside the eye because the index mis-match at the air-cornea interface renders this angle region optically inaccessible from outside the unaltered eye, since any light reflected from the angle region toward the cornea is totally internally reflected at the air-cornea interface. As a result, diagnostics for the outflow pathway in vivo have been limited. Moreover, surgical therapeutics for the outflow pathway in vivo have also been limited to large scale invasive techniques or restricted use of thermal lasers.

With reference to diagnostics, two techniques have been used clinically to evaluate the outflow pathway: tonography and conventional gonioscopy. Tonography involves the continuous measurement of the intraocular pressure over the course of minutes in response to a deforming weight placed on the eye. Due to challenges with both the patient interface and the technical difficulty of this test, tonography is currently rarely used in the clinical setting. In contrast, gonioscopy involves the placement of a special contact lens on the eye to directly visualize the entrance of the outflow pathway from the inside of the eye, and remains a standard component of the glaucoma exam. However, visualizing only the entrance of the outflow pathway informs one only of the patency of the entrance—to distinguish between "open" or "closed" angle glaucomas. No further information about the remainder of the outflow pathway beyond the entrance (such as the trabecular meshwork and Schlemm's canal) is obtained because conventional gonioscopy does not allow for visualization below the tissue surface. These internal structures are the postulated actual sites of outflow resistance.

To view the entire extent of the outflow pathway, a tomographic imaging technique is required, preferably to view the critical structures directly from inside the eye. Optical coherence tomography (OCT) is a non-invasive, micrometer resolution optical imaging technique that has been successfully used in medicine to produce cross-sectional in vivo images of a variety of tissues. In ophthalmology, OCT has become an accepted clinical standard technique for imaging of retinal pathology. OCT is also routinely used for imaging the anterior segment, including the irido-corneal angle in the region of the trabecular meshwork from the outside, in which it is limited to providing gross anatomical views of those structures. The shortcomings of conventional anterior segment OCT for imaging the ocular outflow pathway from outside the eye include loss of signal and resolution by imaging externally through the optically translucent corneal-scleral limbus, and the ability to only measure selected angular location (typically temporal and nasal) limiting complete circumferential analysis. Histologically, the outflow pathway has been shown to vary circumferentially, and limited sampling may not identify the pathologic areas.

To overcome these issues and to maximize the imaging capabilities of OCT for this anatomical region, light would ideally be directed through the optically clear cornea into the internal entrance of the outflow pathway and scanned circumferentially. However, due to the large refractive index change between the corneal surface and the surrounding air, the irido-corneal angle is optically isolated (as a result of total internal reflection), making optical imaging of this area challenging.

As previously described, surgical therapeutics for the ocular outflow pathway in vivo have been limited to large scale invasive techniques or restricted use of thermal lasers. Large scale invasive techniques refer to "scalpel surgeries." In these techniques, the surgeon utilizes a blade to open the ocular outflow pathway. This can be done externally as in trabeculectomy (a punch is used to locally "punch out" the entire outflow pathway in a select region), canaloplasty (an opening is created in the outflow pathway and then a catheter is driven circumferentially around the entire pathway), among other procedures. Internal techniques are also available such as in goniotomy, in which a blade is inserted into the anterior chamber and the internal opening of the outflow pathway is sliced open. These techniques share in common blunt manual dissection of an area that is mere microns in dimension.

Thermal lasers have also been used to surgically manipulate the ocular outflow pathway. These are known as laser trabeculoplasty and use the laser to heat the entrance of the ocular outflow pathway (trabecular meshwork). Typically, the surgeon uses a single faceted mirror to see one area of the trabecular meshwork and apply the laser, the circumferential extent is treated by physically spinning the facet to access the remaining areas. This treatment is primarily superficial; involvement of deeper structures is usually a result of inadvertent thermal/biological changes from the superficial laser treatment.

In an ideal scenario, the precision of the laser would be used to therapeutically change the deeper structures of the ocular outflow pathway. In contrast to "scalpel surgery," this would provide a minimally invasive targeted means of altering any pathologic areas of the outflow pathway.

With an optical system that allows for direct OCT viewing of the ocular outflow pathway from inside the eye to create tomographic images of this area, one would have the ability to visualize the pertinent structures. Because OCT is an optical technique, laser energy can also be delivered via the same optical system. In this way, minimally invasive, image-guided therapeutics of the ocular outflow tract become possible.

Thus, improved optical access to structures of the eye would improve diagnosis and treatment of conditions related to structures inside the eye, especially peripheral structures that have heretofore been difficult to access by direct imaging methods.

SUMMARY

In one embodiment, the invention provides a system for obtaining low-angle circumferential optical access to an eye of a subject. The system includes a light source to generate a beam of light; a beam steering mechanism to steer the beam of light a focusing lens to focus the beam of light; and a contact lens to direct the beam of light into the eye of the subject, the contact lens including a tapered reflective surface to direct the beam of light into the eye of the subject.

In another embodiment the invention provides a method for obtaining low-angle circumferential optical access to an eye of a subject. The method includes steps of generating a beam of light using a light source; steering the beam of light using a beam steering mechanism; focusing the beam of light using a focusing lens; and directing the beam of light into the eye of the subject using a contact lens, wherein the contact lens includes a tapered reflective surface to direct the beam of light into the eye of the subject.

In yet another embodiment, the invention provides a contact lens for obtaining low-angle circumferential optical access to an eye of a subject. The contact lens includes an optically transparent body having a tapered reflective surface; an eye contacting portion at a first end of the body; and a light entry portion at a second end of the body.

Other aspects of the invention will become apparent by consideration of the detailed description and accompanying drawings.

BRIEF DESCRIPTION OF THE DRAWINGS

FIG. 7 shows an embodiment of a contact lens for obtaining low-angle circumferential optical access to an eye of a subject.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The present disclosure provides in part an optical system along with methods that allow for OCT viewing of the ocular outflow pathway from inside the eye to create tomographic images of this area and other areas of the eye. This optical system also allows for full circumferential scanning of the outflow pathway. The optical system can be built either as an add-on accessory to existing commercially-available retinal or anterior segment OCT systems, or can be built as a standalone handheld or portable system. Additionally, methods to analyze and present these images for clinical use are provided. As this system is based on OCT, previously-developed functional OCT techniques such as Doppler or elastography can further extend the platform to allow characterization of flow and resistance through this pathway.

One aspect of the present disclosure provides a system which includes an optical arrangement for delivering a tightly-focused OCT beam from a conventional OCT x-y scan head through the cornea and into the irido-corneal angle in a fully circumferential scannable geometry. To optically image the internal entrance of the ocular outflow pathway through the clear central cornea, one must account for total internal reflection due to the required steep angle of approach and the large index change at the air-cornea interface. Collimated OCT light is directed towards the cornea as in conventional anterior segment OCT. However, a custom focusing contact lens system is introduced to redirect and focus OCT light into the ocular outflow pathway. By placing this contact lens system on the cornea (and directly coupling the contact lens to the patient's eye using a balanced salt solution or similar solution), the large air-cornea index change is eliminated as the index change is greatly reduced, being between several materials having similar indices of refraction, namely the contact lens system, the cornea, and the salt solution. In some embodiments, the saline solution may include so-called 'gel' eye drops which have a lubricant such as carboxymethyl cellulose, hydroxypropyl methyl cellulose, hydroxypropyl cellulose, hyaluronic acid, or other similar polymers found in artificial tears, gels, or ointments.

To obtain continuous scanning around the entire ocular outflow pathway, which has a circular geometry, and to achieve the steep angle of approach required to observe the pathway, the resulting geometry for a contact lens reflector in various embodiments includes a tapered surface. The tapered surface of the contact lens may have a straight or curved profile, or combinations of different profile shapes and angles, and may include frustoconical and/or parabolic shapes.

Figure 1:
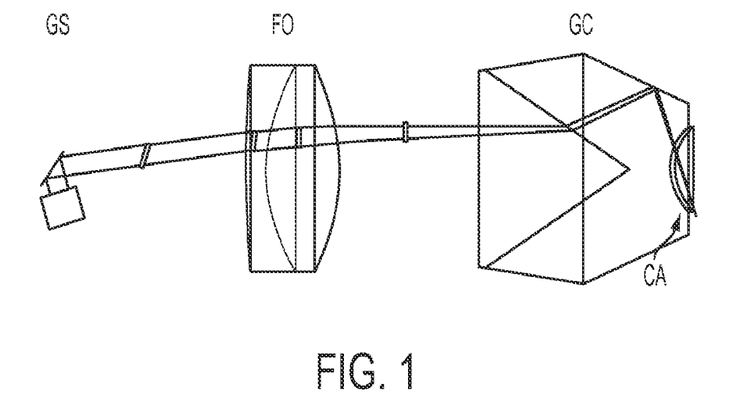
FIG. 1 is a ZEMAX ray trace diagram showing three basic elements of a low-angle circumferential optical access system including a beam steering mechanism, a focusing lens, and a contact lens.

For the straight-profile frustoconical shape, each point along the surface varies in positive focusing power depending of the radius of the cone at the incident position of the beam. This positive focusing, however, occurs only in a single dimension, resulting in an astigmatism whose angle is dependent on the azimuthal angle of the cone on which the beam is incident. Thus, in one embodiment, to correct for these astigmatisms, a second cone that has negative focusing power can be placed in front of the reflective cone (FIG. 1). This combination of two conical shapes for directing the beam of light to the eye generally reduces the overall error due to astigmatism.

Figure 8:
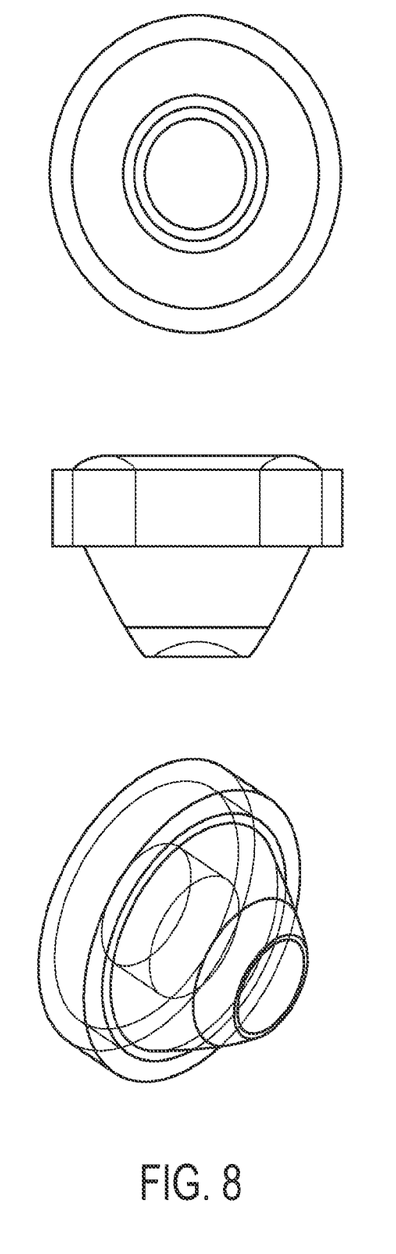
FIG. 8 shows a contact lens having a frustoconical reflective surface and a hemitoroidal refractive surface at the point of light entry.

In other embodiments including those described further below, instead of a negative focusing power cone, the point of light entry on the contact lens includes a convex surface through which the beam of light enters the contact lens. The convex surface in one particular embodiment is a hemitoroidal projection (FIG. 8). In another embodiment, the point of light entry is an annular aspheric surface (FIG. 7).

Another aspect of the present disclosure provides methods for scanning the OCT beam in an efficient manner, e.g. in radial-priority or circumferential-priority, to generate useful clinical output in minimum imaging time. In various embodiments, the beam of light is moved using a beam-steering mechanism (e.g. galvanometers or other mechanisms) to reach a particular location on the eye. An A-scan is obtained at the location (to provide depth information), after which the beam is moved to another location to obtain another A-scan, a procedure that is repeated for a series of locations of the eye. The information from a plurality of A-scans is then combined to generate an image or portion of an image. The beam may be scanned in a number of different patterns, including radial or circumferential, which may encompass varying portions of the eye. In some embodiments, data may be collected from the entire circumference of the eye and in other embodiments data may only be collected from a portion or portions of the eye, for example a region of particular interest for diagnosis and/or treatment of a patient.

The outflow pathway may be scanned with circumferential or radial (i.e. cornea to iris) priority to create a given B-scan. Subsequent B-scans may be scanned in the other direction (radial or circumferentially) to create a tomographic volumetric representation of the ocular outflow pathway.

Other embodiments of the present disclosure provides methods for segmenting, processing, and displaying the resulting image dataset in a way most readily understandable and useful to clinicians. The collected images are segmented using methods such as intensity segmentation, graph techniques with dynamic programming, or others to identify regions of interest including the trabecular meshwork (TM) and Schlemm's canal (SC). Morphometric parameters that have histologically been correlated with glaucoma (e.g. thickness of the TM and size of the SC) can then be displayed either directly or symbolically for clinical interpretation. Additional parameters depending on the OCT technique used can also be shown similarly (flow, elastography). In various embodiments, in addition to the optical system for circumferential scanning of the ocular outflow pathway to provide diagnostic images, the system also includes an optical system for delivering therapeutic light, for example using a laser platform.

Figure 2:
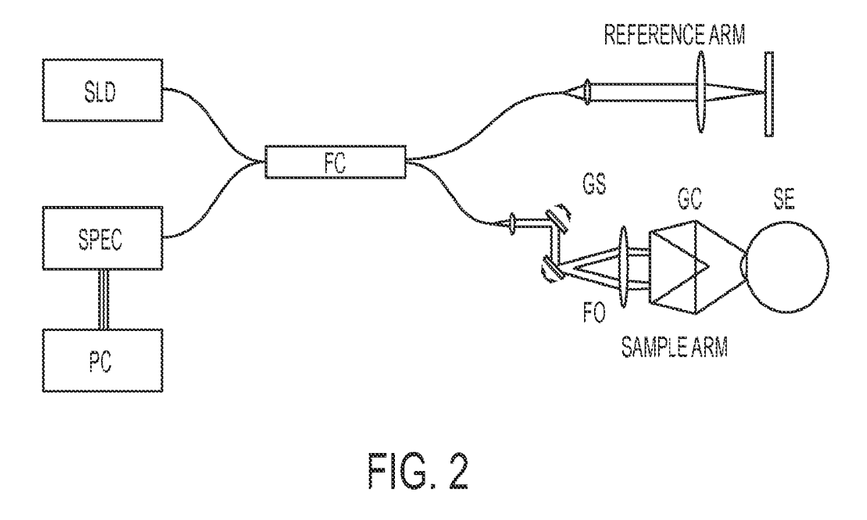
FIG. 2 shows a high-level diagram of a spectral domain implementation of gonioscopic OCT.

The optical system according to one embodiment of the present disclosure, which is based on scanning a single spot around the ocular outflow pathway, includes three distinct components. The first component, the beam steering mechanism, provides the ability to scan a single beam of collimated light in two dimensions. The second component, the focusing lens, is the need to focus the collimated beam after the scanning of the beam. The final component, provided by the contact lens, achieves the steep angle required to observe the ocular outflow pathway. Any or all of these components could potentially be combined to achieve the desired results. A high-level schematic of a spectral domain implementation of gonioscopic OCT is shown below in FIG. 2, although in other embodiments gonioscopic OCT can be extended to any OCT implementation (including time domain and Fourier domain OCT).

FIG. 1 shows an embodiment of an optical system including a contact lens for obtaining low-angle circumferential optical access to an eye of a subject. For simplicity, in the design of FIG. 1, each component is depicted as a separate optical device. Nevertheless, the simplified system of FIG. 1 could be expanded with a more complex system of lenses and other components and/or through the use of focusing mirrors.

The optical system includes a beam steering mechanism (shown schematically on the left side of FIG. 1) having a pair of mirrors mounted on orthogonal axis galvanometers. In other embodiments, the beam steering mechanism may include, but is not limited to, mirrors that can pivot in two axes, rotating prism pairs, acousto-optic deflectors, resonant scanning mirrors, rotating polygonal scanning mirrors, and microelectromechanical system (MEMS) based scanning devices.

The focusing objective depicted in FIG. 1 may be a single radially symmetric achromatic lens which provides the entirety of the necessary focusing power of the system, or this functionality may be provided by two or more focusing lenses.

The final element of the system requires a method to achieve the steep angle of incidence required for imaging the outflow pathway. This unfortunately cannot be done using a simple air-to-cornea interface due to total internal reflection and therefore requires an adapter. In the system shown in FIG. 1, this adapter or contact lens has a single piece of poly(methyl methacrylate) (also known as PMMA or acrylic) coupled to the cornea with balanced salt solution or other similar compound(s). PMMA was chosen as the material for many reasons including better index matching between contact and cornea than most types of glass, ease of manufacturing, high Abbe number (which relates to a low chromatic dispersion value), and because the material is strong and lightweight. Nevertheless, in some embodiments other materials such as glass may be used. In one embodiment, N-FK51A (Schott) glass is used, allowing for lower chromatic dispersion. In other embodiments, the contact lens may be made using a plastic such as Zeonex E48R or inorganic crystals such as calcium fluoride ($CaF_2$)

In the contact lens shown in FIG. 1 has several unique features, the beam entrance consists of a negative cone (or axicon) shape. This shape helps to steer the beam at a steep angle away from the optical axis and also provides negative astigmatism compared to a flat entrance; this astigmatism is dependent on both distance from the cone apex and the radial angle of the beam entrance. Once the beam has entered the PMMA, it is angled such that when it hits the next surface, it does so at greater than the critical angle resulting in total internal reflection. Using this reflection negates the need for a metal mirror as a reflector to achieve the desired steep incidence angle for imaging the ocular outflow pathway. Nonetheless, in various embodiments, the tapered reflective surface of the contact lens may be coated with a reflective material including a metal such as gold, silver, aluminum, or a dielectric material to improve reflectivity.

Figure 3:
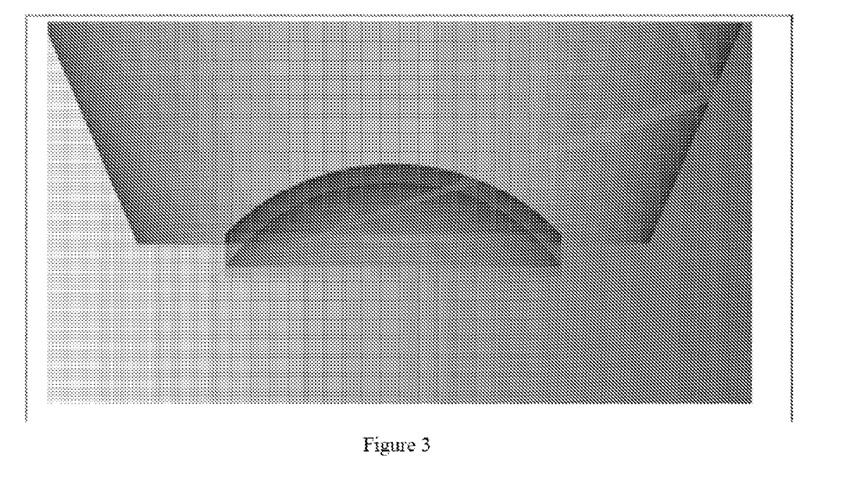
FIG. 3 shows a close-up view of the interface between a contact lens and the cornea of a subject, including a ray-trace showing the path of light reflecting off the tapered surface of the contact lens and crossing into the cornea through a coupling fluid.

The contact lens also includes at one end a concave surface or well for placement of the subject's cornea along with the coupling solution. In one embodiment the concave surface has a spherical radius of curvature of 7.4 mm to match that of typical corneas. In other embodiments, the concave surface may have other sizes and shapes to accommodate various subjects' corneas. In various embodiments, the region of the contact lens outside of the concave well includes a lip to provide mechanical support and stabilization such that sliding of the contact is minimized during image acquisition. A ray trace diagram showing in detail the reflection from the tapered reflective surface (including the total internal reflection) within a contact lens made of PMMA as well as the effect of the index matching between the contact and cornea is shown in FIG. 3.

Given an optical system which delivers a tightly focused, scannable spot through the transparent cornea into the irido-corneal from the inside of the eye, as described above, this optical system can be utilized to perform tomographic scanning of the outflow pathway within the angle region with optimal coverage (not missing any critical structures) and efficiency (scan time).

Figure 4:
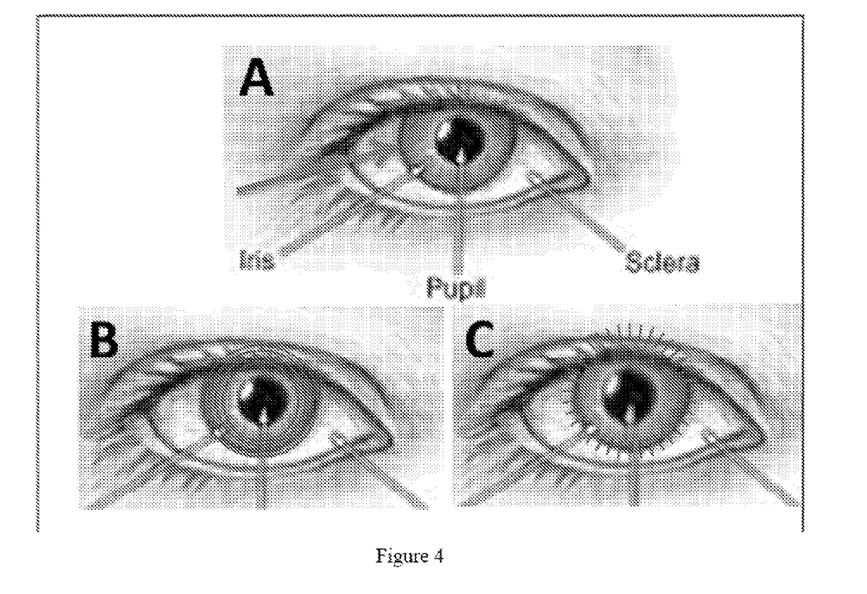
FIG. 4A shows the appearance of the iris, pupil, sclera, and irid-corneal angle in the eye of a subject.
FIG. 4B shows a circumferential-priority scan pattern in which only a representative number of scans is shown.
FIG. 4C shows a radial-priority scan pattern in which only a representative number of scans is shown.

Two basic scan patterns for examining the outflow pathway from inside the eye are disclosed in FIG. 4. Both scan patterns are defined with respect to standard OCT imaging terminology, wherein an A-scan represents a single depth-resolved axial reflectivity map, a B-scan generally refers to a two-dimensional cross-sectional image constructed from a series (typically 100-1000) of laterally-displaced A-scans which can be viewed as an image, and a volume scan represents a three-dimensional dataset typically constructed from a sequence (typically 100-1000) of azimuthally displaced B-scans. FIG. 4A shows the structures of the eye of a subject. The circumferential-priority scan pattern, illustrated in FIG. 4B, is comprised of one or more B-scans obtained while scanning the focused spot in a circular pattern around the circumference of the irido-corneal angle. If the subject's eye remains sufficiently stationary, a single or a few sequential circumferential B-scans may be positioned to view the entire circumference of circular structures such as Schlemm's canal. More practically, a series (10-1000) of sequential circumferential-priority scans with different radii may be obtained in order to collect a volume of data including all relevant outflow structures. The advantages of circumferential-priority scanning include maximum continuity of image integrity for circular structures; however, the primary drawback of this scan pattern lies in its sensitivity to patient motion.

An alternative scan pattern is the radial or partial radial scan pattern illustrated in FIG. 4C. In this pattern, a sequence of one or more relatively short radially oriented B-scans are obtained in a circular pattern around the circumference of the irido-corneal angle. The individual radial B-scans may extend all of the way to the center of cornea, as in a conventional radial OCT scan pattern; however, the pattern will be more efficient if only the relevant parts of the radial profiles are scanned. The principle advantage of the radial scan pattern is that local segments of the irido-corneal tomographic data sets will be relatively free of motion artifacts since they are acquired in rapid sequence.

Once the images are acquired, regions of clinical interest may be identified and displayed for clinical interpretation. For illustrative purposes, morphometric analysis of Schlemm's canal will be described here, as dimensions of this canal have been correlated with glaucoma in histologic studies. However, other anatomic components of the outflow pathway including but not limited to trabecular meshwork and its subcomponents, collector channels, and distal vessels may also be imaged and treated similarly as in this illustrative example. Analyses also do not have to be limited to morphometric examination; functional investigations available on the OCT platform can be made available to the trabecular meshwork with this design.

For morphometric analysis of Schlemm's canal, the structure is first identified. Anatomically, Schlemm's canal is located distal to the trabecular meshwork (where proximal is the anterior chamber and the superficial cornea is distal to Schlemm's canal). Because of this relationship to the trabecular meshwork, the search region can be limited to the termination of Descemet's membrane anteriorly and the iris root posteriorly, both identifiable structures on OCT.

In this region, Schlemm's canal is seen as a hyporeflective area in OCT as it is a fluid-filled structure, in contrast to the surrounding tissue. Using desired manual and/or automated image processing segmentation techniques (e.g. threshold, graph cut, edge detection, region growing, and others) including any requisite preprocessing, Schlemm's canal is identified in each individual image of the volumetric acquisition.

Once identified, Schlemm's canal is removed from the surrounding image and can simply be displayed in isolation three-dimensionally. To improve the clinical utility of this information, though, dimensions of the canal can be extracted and morphometric parameters computed. These parameters can be local, e.g. diameters at various locations around the canal, as well as global, e.g. volume of the entire canal. The morphometric parameter can then be compared to a reference value such as the canal maximum or against a normative database.

Figure 5:
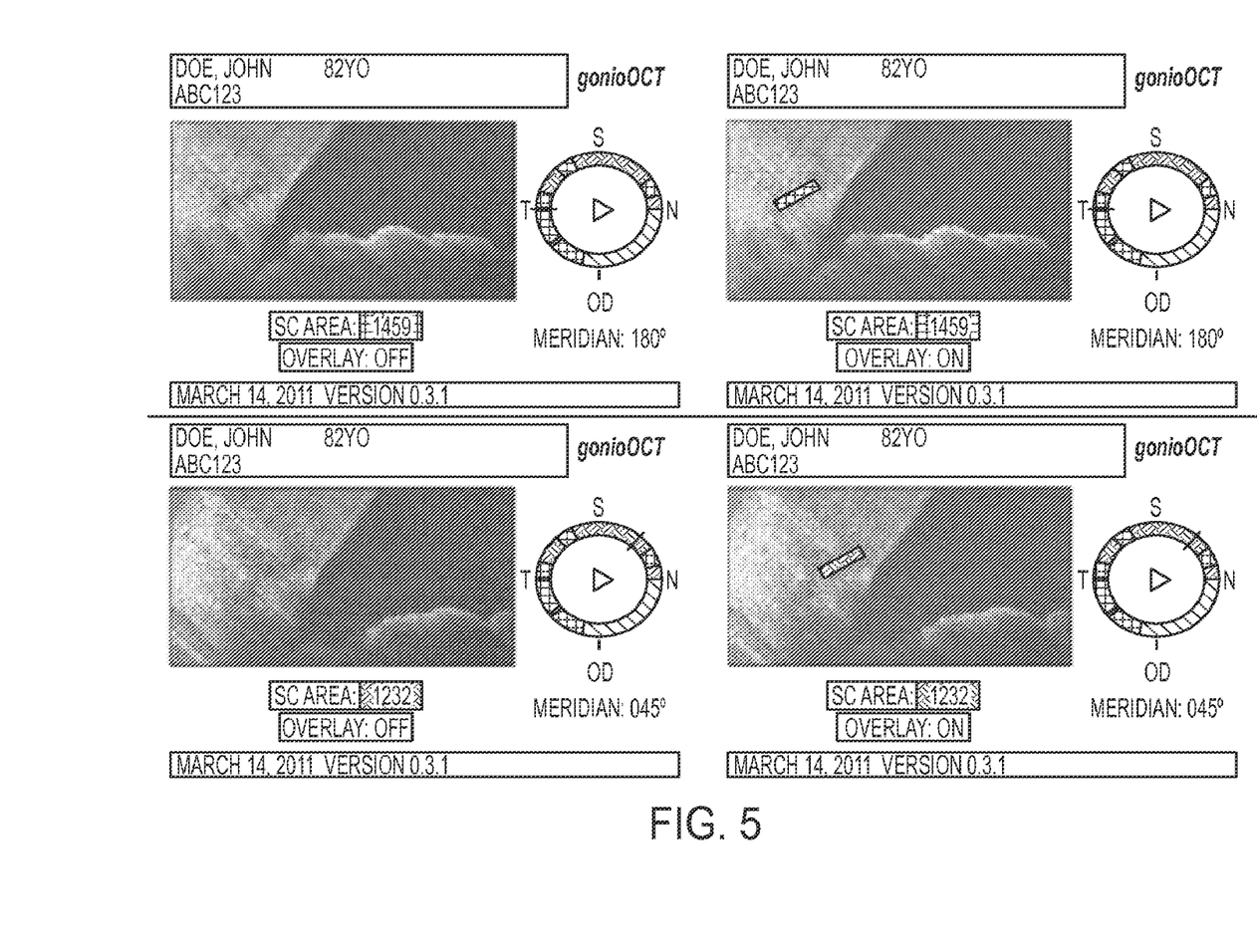
FIG. 5 shows several screenshots of a clinical data analysis system.

FIG. 5 shows a sample output from an OCT scan of the outflow pathway highlighting Schlemm's canal, presented as a series of screenshots. In each screenshot, the acquired image is on the left. On the right is a symbolic map showing the location of the image along the circumference of the canal. The area of the canal in that particular "slice" of the canal is displayed underneath the image. The symbolic map also color codes this area as compared against the canal maximum. In this particular example, yellow means the area is <50% of the canal maximum and red means the area is <25% of the canal maximum. Using an overlay, the segmented Schlemm's canal can also be shown to the user. With this display, the captured image is readily available to the clinician, but for ease of use, the symbolic map also quickly signals to the clinician the areas which may be pathologic. In this particular example, a surgeon planning on inserting an outflow bypass device can now know which areas of the canal are likely nonfunctional and will likely benefit from the bypass (versus the current standard of simply placing it in a random quadrant).

Similar segmentations, analyses, and displays can also be performed for other ocular outflow substructures and gonioscope OCT data. Multiple analyses could also be displayed in a single screen (adding another concentric circle to the above symbolic map indicating trabecular meshwork thickness, for example).

Yet another aspect of the present disclosure provides a device and system that incorporates a continuous scan circular mirror. Such a system includes an optical system for circumferential scanning of the ocular outflow pathway to provide diagnostic images and a therapeutic laser platform. One embodiment provides for a combination of the circumferential scanning optical system described herein for optical coherence tomography (OTC) imaging along with an ophthalmic femtosecond laser. The ophthalmic femtosecond laser in one embodiment may be an infrared laser (~1040 nm) that creates precise cleavage planes in tissues via photodisruption. Currently, it is used for creating corneal lamellar flaps at desired depths as would be used in laser refractive surgery.

In one embodiment, the optical system is applied to the eye and a circumferentially scanned OCT image is obtained of the ocular outflow pathway. As the site of ocular outflow resistance is thought to be at the interface between the trabecular meshwork (TM) and Schlemm's canal (SC), this region would be identified in the image either manually or automatically. Using this image guidance, the ophthalmic femtosecond laser would then be used to open the TM-SC interface circumferentially around the eye by focusing therapeutic laser energy in that specific region via the same optical system used to deliver infrared OCT light for diagnostic purposes. OCT imaging can be used in a concurrent, interlaced fashion or sequentially to monitor the progress of the therapeutic laser. By precisely removing the TM-SC interface, the major site of ocular outflow resistance can be eliminated without disrupting surrounding tissues as would occur with a manual blade or current trabeculoplasty lasers.

Figure 6:
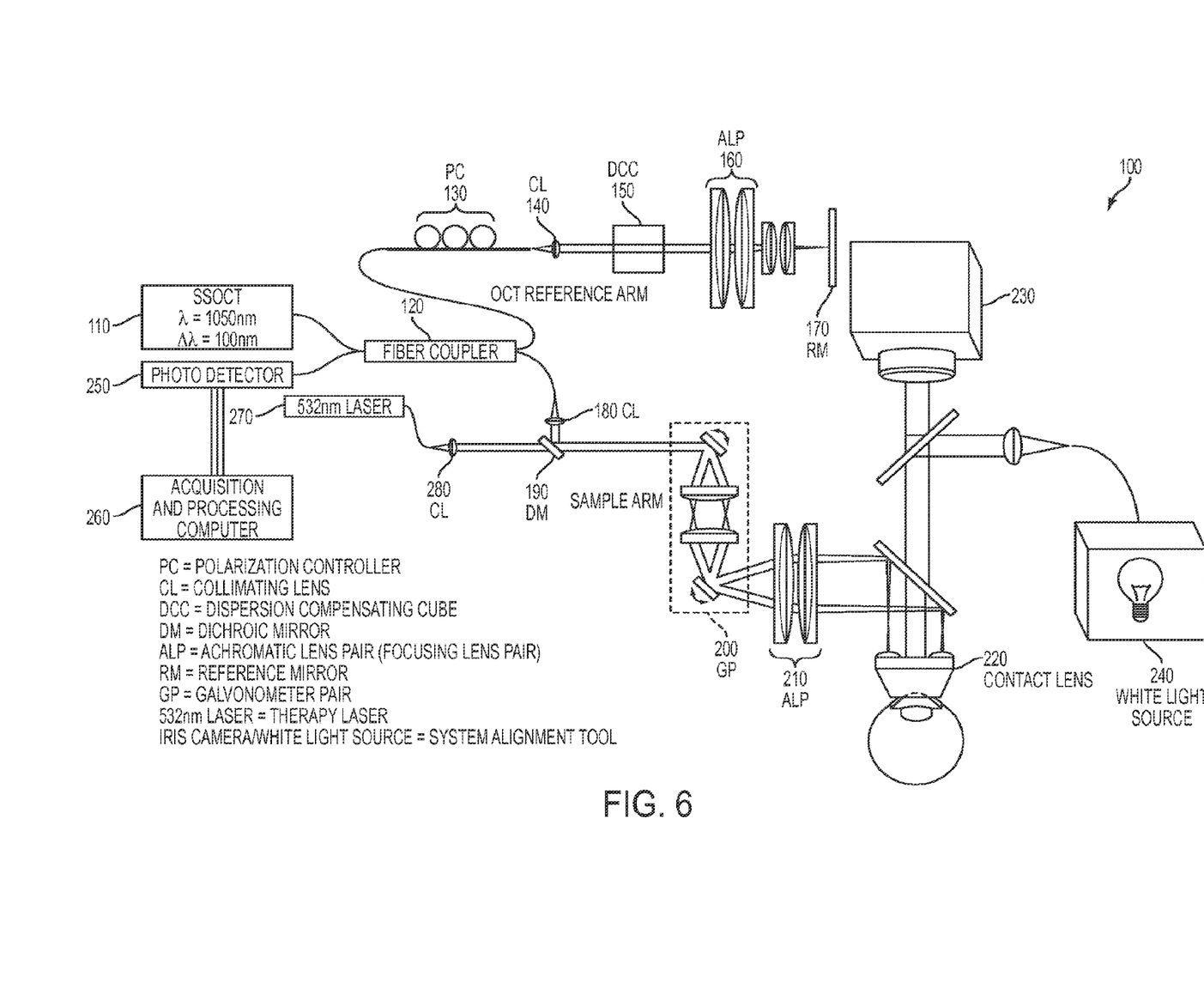
FIG. 6 shows an embodiment of a system for obtaining low-angle circumferential optical access to an eye of a subject.
Figure 7A:
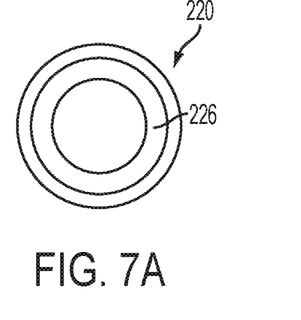
FIG. 7A is a front view.
Figure 7B:
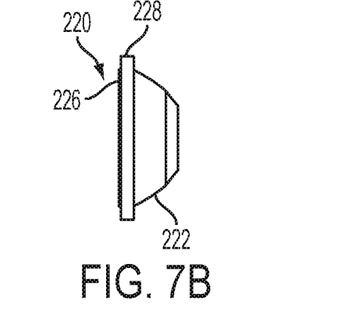
FIG. 7B is a side view.
Figure 7C:
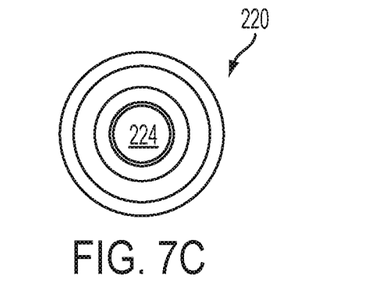
FIG. 7C is a rear view.
Figure 7D:
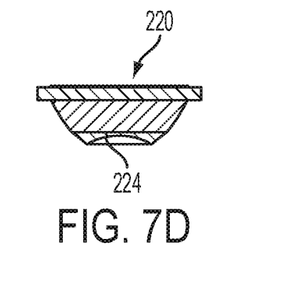
FIG. 7D is a cross-sectional view through the line B-B shown in FIG. 7E.
Figure 7E:
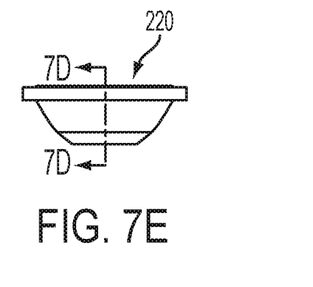
FIG. 7E is another side view.
Figure 7F:
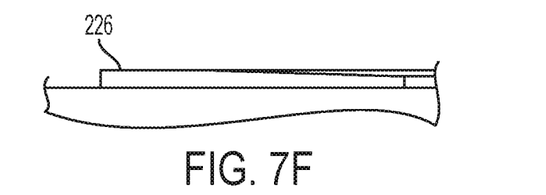
FIG. 7F is a close-up view of the aspheric annular surface.

FIG. 6 depicts another embodiment of a system 100 for obtaining low-angle circumferential optical access to an eye of a subject. The system includes a light source 110 and a fiber coupler 120. In the depicted embodiment, the fiber coupler 120 splits the light from the light source 110 and sends a portion to a reference arm and another portion to a sample arm as part of an OCT system. The reference arm of the depicted embodiment includes a polarization controller 130, a collimating lens 140, a dispersion compensating cube 150, an achromatic lens par/focusing lens pair 160, and a reference mirror 170. The sample arm includes a collimating lens 180, a dichroic mirror 190, a beam steering mechanism 200 (which may include a galvanometer pair as shown), an achromatic lens par/focusing lens pair 210, and a contact lens 220. The depicted embodiment of the system 100 also includes an iris camera 230 and white light source 240, along with suitable optical components, to be used as part of an alignment system. The light source 110 can include a swept-source OCT (SSOCT) laser centered at λ=1050 nm with Δλ=100 nm, although other types of sources are also possible. In some embodiments, the light source 110 may include any spatially coherent broadband visible or near-infrared light source operated with an axial scan rate from 10 Hz to 10 MHz, where the bandwidth may vary from 10 nm to hundreds of nanometers. In other embodiments, the light source 110 may include superluminescent diodes having center wavelengths including but not limited to 830 nm, 1050 nm and 1310 nm. In yet other embodiments, the light source 110 may include a Fourier-domain mode locked (FDML) laser having a center wavelength such as 1050 nm or 1310 nm. In still other embodiments, the light source 110 may include a vertical-cavity surface-emitting laser (VCSEL) having a center wavelength such as 1050 nm or 1310 nm. In further embodiments, the light source 110 may include a femtosecond laser such as a titanium-sapphire (Ti—AlO$_3$) laser or a supercontinuum laser. The center wavelengths may vary from the stated center wavelength values, for example in certain embodiments by approximately ±40 nm for at least some of the light sources 110 listed above.

Also coupled to the fiber coupler 120 is a photo detector 250 which in turn is connected to an acquisition and processing computing system 260. In certain embodiments, the photo detector 250 collects light from a series of A-scans which contain depth information for a given point on the sample and this A-scan information from several points on the sample is then processed by the acquisition and processing computing system 260 to produce images. The images are then analyzed, stored, and/or displayed to a user.

An additional feature of the depicted system 100 is a therapeutic light delivery arm, which in the depicted embodiment includes a light source 270, e.g. a 532 nm laser source, and suitable optical coupling components 280, e.g. a collimating lens, for tissue ablation and other treatments. The therapeutic light source 270 may include lasers or other light sources in the UV, visible, or infrared portions of the spectrum.

Subjects may include humans and other primates as well as laboratory research subjects such as mice, rats, and rabbits. Embodiments of the disclosed system 100 can be used to view and/or treat structures of the eye that are difficult or impossible to access using other techniques, including the iridocorneal angle and peripheral regions of the retina.

FIGS. 7A-7F show an embodiment of a contact lens 220 for use with the system 100. As discussed above, the contact lens 220 may be fabricated from a number of optically transparent materials including glass or PMMA. The contact lens 220 includes a tapered reflective surface 222 which may be a composite having several segments each with a different shape (e.g. parabolic or frustoconical) and/or taper angle; in the embodiment shown in FIG. 7, the reflective surface 222 has a parabolic cross section.

The front surface of the contact lens 220 includes an aspheric annular surface 226 (FIG. 7F) through which light enters the contact lens 220. The aspheric annular surface 226 corrects for the astigmatism would otherwise be introduced by the parabolic reflective surface 222. In certain embodiments, all or a portion (e.g. the aspheric annular surface 226) of the front surface of the contact lens 220 may be coated with an antireflective coating. As discussed above, the reflective surface 222 may have a reflective coating applied thereto.

The contact lens 220 includes a concave surface 224 to fit into the cornea of the eye of the subject. The concave surface 224 can have various sizes and shapes to accommodate various subjects' corneas. The contact lens 220 can also include an outer rim 228 for mounting, e.g. to a bore.

Figure 9:
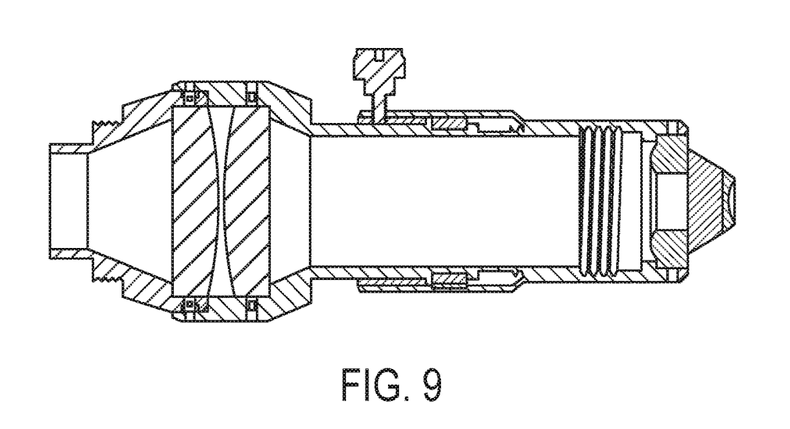
FIG. 9 shows a gonioscopic bore which allows for fine control of astigmatism correction.
Figure 10:
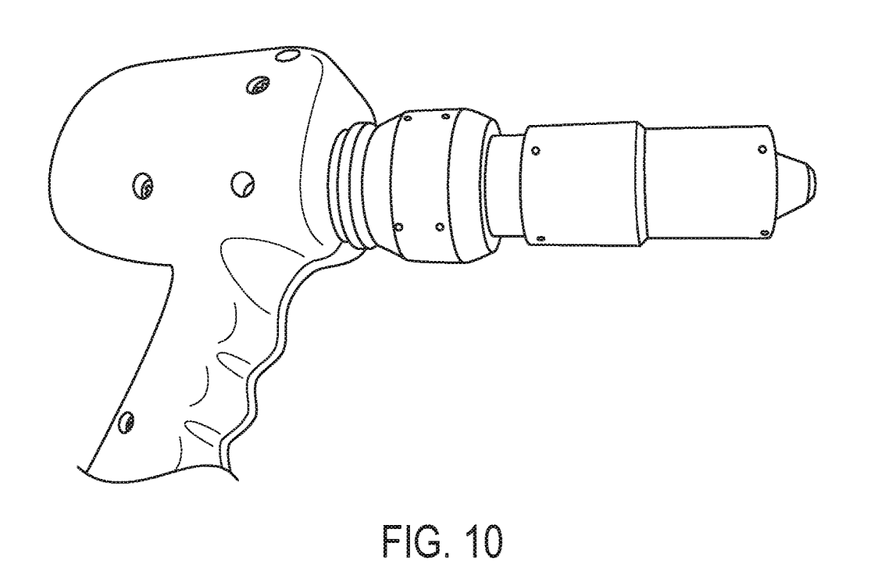
FIG. 10 shows a bore attached to a hand held probe.

FIG. 8 shows an embodiment of a contact lens having a frustoconical reflective surface and where the front surface includes a hemitoroidal refractive surface which corrects for the astigmatism introduced by the frustoconical reflective surface. FIG. 9 shows a gonioscopic bore, including a focusing lens pair and a contact lens, which allows for fine control of astigmatism correction by facilitating fine control of the distance between the focusing lenses and the contact lens, which in turn adjusts the imaging properties of the contact lens. FIG. 10 shows a bore such as that shown in FIG. 9 attached to a hand held probe.

Thus, the invention provides, among other things, methods and systems for obtaining low-angle circumferential optical access to the eye. Various features and advantages of the invention are set forth in the following claims.

What is claimed is:

1. A system for obtaining low-angle circumferential optical access to an eye of a subject, the system comprising:
   a light source to generate a beam of light;
   a beam steering mechanism to steer the beam of light;
   a focusing lens to focus the beam of light; and
   a contact lens to direct the beam of light into the eye of the subject, the contact lens including
      a refractive surface through which the beam of light enters the contact lens, and
      a tapered reflective surface to direct the beam of light into the eye of the subject such that circumferential optical access is obtained by adjusting a steered position of the beam of light, wherein the tapered reflective surface is radially symmetric about a central axis, wherein the refractive surface is shaped to refract the beam of light entering the contact lens through the refractive surface at an angle away from the central axis and towards the tapered reflective surface, and wherein the reflective surface reflects the refracted beam of light towards the central axis and into the eye of the subject.

2. The system of claim 1, further comprising a detector to detect light reflected from the eye of the subject.

3. The system of claim 1, wherein the refractive surface of the contact lens includes a tapered annular aspheric surface through which the beam of light enters the contact lens, wherein the tapered annular aspheric surface is radially symmetric about the central axis of the contact lens.

4. The system of claim 1, wherein the contact lens comprises an optically transparent material and wherein the tapered reflective surface of the contact lens has a reflective material applied thereto.

5. The system of claim 1, wherein the beam steering mechanism comprises at least one galvanometer.

6. The system of claim 1, wherein the focusing lens comprises a focusing lens pair.

7. The system of claim 1, wherein the beam of light is directed to the iridocorneal angle of the eye of the subject.

8. The system of claim 1, wherein the contact lens is coupled to the eye of the subject using a saline solution.

9. The system of claim 1, further comprising a therapeutic light source for generating a beam of therapeutic light, wherein the beam of therapeutic light is directed through the contact lens into the eye of the subject.

10. The system of claim 1, wherein the light source comprises a therapeutic light source.

11. The system of claim 1, wherein the tapered reflective surface has a shape selected from frustoconical and parabolic.

12. The system of claim 1, wherein contact lens is configured such that the beam of light reflected internally by the tapered reflective surface remains internal to a material of the contact lens until exiting the contact lens into the eye of the subject.

13. The system of claim 1, wherein the tapered reflective surface includes a frustoconical exterior surface of the contact lens, wherein the refractive surface includes a tapered frustoconical interior surface of the contact lens.

14. The system of claim 1, wherein the tapered reflective surface provides a positive focusing of the beam of light that varies as the beam of light contacts different points along the tapered reflective surface, and wherein the refractive surface is shaped to provide a negative focus of the beam of light to counteract the positive focusing caused by the tapered reflective surface.

15. The system of claim 1, wherein the refractive surface of the contact lens includes a convex surface through which the beam of light enters the contact lens.

16. The system of claim 15, wherein the convex surface includes a hemitoroidal projection positioned on a surface of the contact lens opposite the eye of the subject.

17. The system of claim 1, wherein the beam of light is divided into a sample arm and a reference arm and wherein the sample arm is directed to the beam steering mechanism and the reference arm is directed to a reference mirror.

18. The system of claim 17, wherein light returned from the sample arm is combined with light returned from the reference arm to produce an interference signal.

19. The system of claim 18, wherein the interference signal is detected by the detector.

20. The system of claim 18, wherein the interference signal from a plurality of locations on the eye of the subject is combined to produce at least one image.

* * * * *